United States Patent [19]

Latorre

[11] 4,150,669

[45] Apr. 24, 1979

[54] APPARATUS FOR EFFECTING AND ENHANCING AN ERECTION

[76] Inventor: Alvaro Latorre, 721 Cervantes, El Paso, Tex. 79922

[21] Appl. No.: 778,048

[22] Filed: Mar. 16, 1977

[51] Int. Cl.² .......................... A61F 5/00; A61M 5/00
[52] U.S. Cl. .................................... 128/79; 128/214.2
[58] Field of Search ................... 128/79, 214.2, 214 R, 128/215

[56] References Cited

U.S. PATENT DOCUMENTS 3,552,394  1/1971  Horn .................................. 128/214.2
4,009,711  3/1977  Uson ....................................... 128/79

Primary Examiner—Lawrence W. Trapp
Attorney, Agent, or Firm—Bruce Newell

[57] ABSTRACT

A dual hypodermic needle syringe for injecting fluids into the penis, having two parallel, interconnected barrels connected to needles extending from the barrels. Plungers in the barrels are activated simultaneously by moving a single depressor. An appropriately sized, typically curved end member is attached to or integrally molded into the body portion of the barrels. The end member limits the depth of insertion of the needles.

7 Claims, 7 Drawing Figures

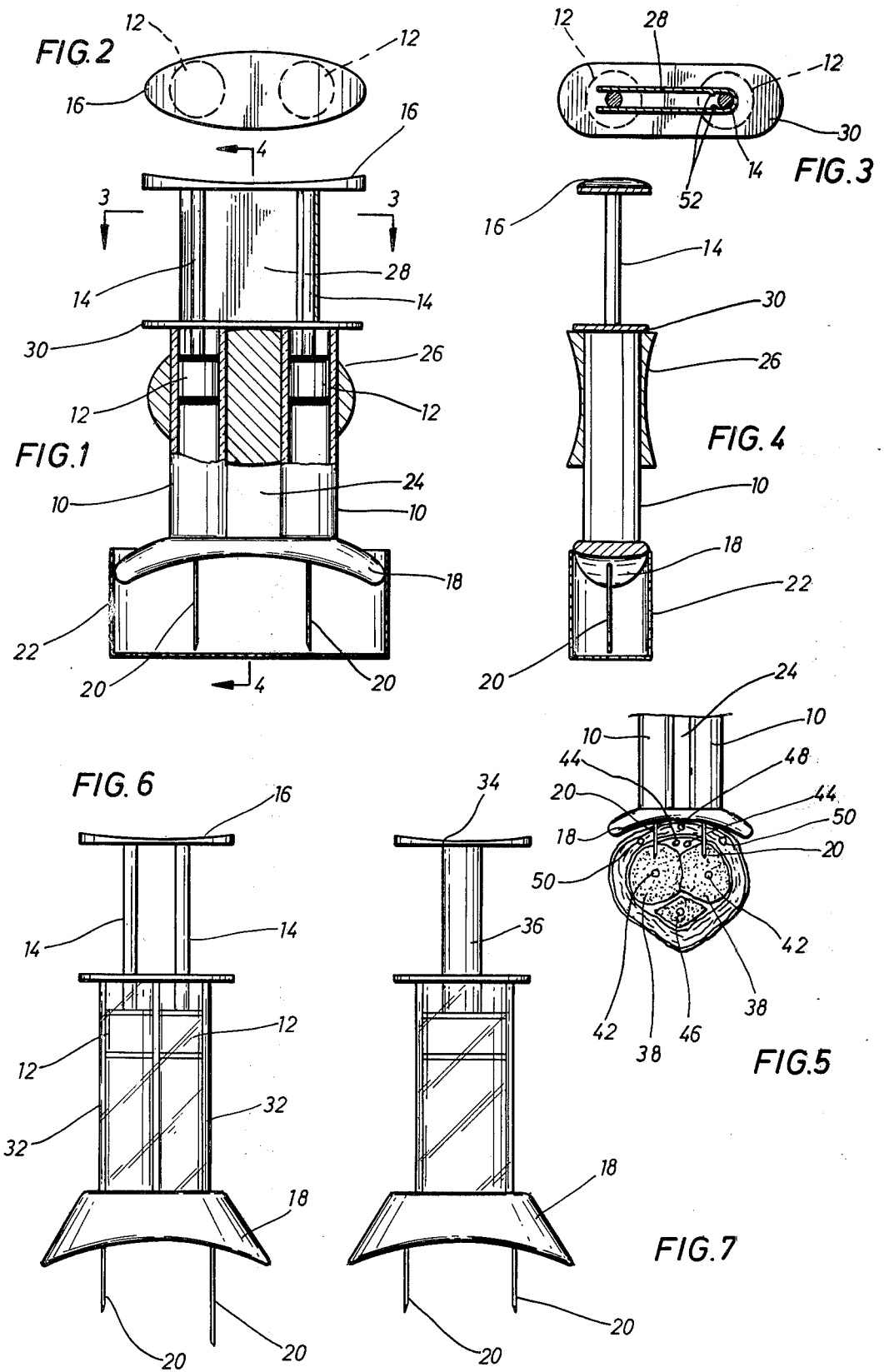

APPARATUS FOR EFFECTING AND ENHANCING AN ERECTION

BACKGROUND OF THE INVENTION

This invention relates to multiple hypodermic needle syringe arrangements, more particularly, to a dual needle syringe for use in simultaneously injecting certain tissues in the penis, in connection with a method for alleviating and treating male impotence by aiding in producing, enhancing, and sustaining an erection of the penis.

The ability to attain and maintain an adequate erection has long been a problem to older men as well as to some younger men experiencing psychogenic or physiologic impotence due to various factors. This invention is the instrumentality used in connection with the first really viable solution to this problem, a solution involving no tourniquets, straps, bands, sleeves, or other supportive devices used in the past to aid in effecting an erection.

Whether the impotence is absolute (involving all sexual modalities), total (also affecting all sexual functions, though not necessarily libido), or partial (affecting the rigidity or duration of erection), or whether the cause of impotence is organic (due to structural changes, disease, or some demonstrable functional impairment anywhere in the sexual system), psychogenic (due to psychological factors such as depression or aversion to a particular sex partner), or physiologic (due to old age or sexual satiation), the result is the same: inability to engage in sexual activity due to the lack of an adequate erection. Impotence may be defined more fully, however, as the inability to develop or sustain an erection of the penis sufficient to conclude coitus or orgasm and ejaculation to the male's own satisfaction. Impotence treatment methods are generally, however, concerned with the erection aspect and not ejaculatory impotence, which is relatively rare. The penis becomes erect when certain tissues (e.g., the corpora cavernosa, 38 in FIG. 5) in the central portion of the penis become widely dilated with blood, thereby causing them to become less flaccid, and in turn causing an erection.

Many devices have been proposed for producing and enhancing an erection, typically by some means of exogenous nervous stimulation of the organ to produce an erection by, for example, local stimulation via vibration, or by blood constrictive devices such as adjustable tourniquet-like rubber band devices which are designed to fit tightly around the shaft of the penis and thereby restrict the flow of blood from the penis through the surface veins, as well as the deeper dorsal vein, to prolong an erection. For example, Atchley U.S. Pat. No. 3,636,948 discloses an adjustable device designed to fit the contour of the penis, to exert greater pressure on the area where the subcutaneous (surface) veins are located, thereby restricting the blood exiting the penis through the peripheral veins. Miller U.S. Pat. No. 2,818,855 is ineffective for depressing the deep dorsal vein and preventing or significantly restricting flow of blood there. There have been numerous other attempts to solve the problem, but all exhibit various disadvantages to the user, and sometimes to the female, such as extreme discomfort during intercourse, to the extent that users might not achieve the desired usefulness as frequently as and to the extent preferred. All the external devices previously proposed have the psychological disadvantage of being an impediment to the sex act, and the operational disadvantage that their duration of effectiveness is relatively short.

What is needed is a way to produce and enhance and even maintain an erection without the attendant difficulties inherent in a device or appliance that must be worn during intercourse. The subject invention, involving nothing which may be annoying or even apparent to the female sex partner, provides such a way be means of a dual needle hypodermic syringe used to inject certain drugs into the penis, thereby allowing for treatment of the tissues which really produce the erection—a significant improvement over treatment of the skin surface with creams or rubbing compounds. The dual needle arrangement is apparently desirable because of the need to inject the corpora cavernosa tissues.

The basic concept of the dual needle syringe is old, and numerous patents have been granted on various devices, for example, Horn U.S. Pat. No. 3,552,394, which discloses a dual hypodermic syringe with integrally molded barrels and independent plungers and needles, apparently of the conventional variety. The Horn device, like other known dual hypodermic syringes, is, however, not suitable for the purpose for which the subject invention is intended. While the spacing of the needles of the Horn '394 syringe could be adjusted to be optimum for the purpose of injecting the penis with an appropriate drug, there is no stop on the base of the barrels as in the subject invention, and the plungers are independently movable. Independently movable plungers will work in the subject invention, but are more difficult to handle. A dual hypodermic syringe for the purposes discussed herein, for use by the general public, should be easy and safe to use, and should be inexpensively manufacturable.

Multiple hypodermic syringe arrangements generally have the same basic characteristics: two (or more) needles which are essentially parallel to one another, and connected to spaced barrels in which plungers, generally independent of one another, are moved to force the fluid through the barrel and, in turn, the needle. The needle diameters and lengths vary, depending on the type of liquid to be injected and the tissue in which the liquid in each barrel is to be injected. For example, a short needle is used if the injection is to be subcutaneous, whereas a longer needle is used for an intramuscular injection, or in the case of the subject invention, an intra-corpora cavernosa injection. Where multiple injections are to be made in close areas, it's desirable to make the injections simultaneously, as the patient will experience only one sensation of pain if the distance between the two needles does not exceed the distance at which the surface pain sensors of the skin can distinguish between single and multiple locations of pain. The two-point sensation of pain distance varies over different parts of the body. In some parts of the body, for example, the thigh and upper arm, the two-point threshold of pain may involve a distance of up to 68 mm, whereas the two-point threshold of pain distance on the penis is much smaller, thus necessitating a very close needle arrangement. Needles as small as possible to pass the fluids to be injected should be used to minimize the pain.

The subject invention surpasses the general characteristics of these arrangements and is easy and safe to use, as the curved end member comfortably limits the depth of insertion of the needles, which are as close and as small as possible.

SUMMARY OF THE INVENTION

Essentially, the invention is a dual hypodermic syringe for injecting fluids into the penis. The syringe has two essentially parallel, interconnected barrels having open and closed ends. The closed ends have passageways through them to the needles, which are attached to the barrels at their closed ends. The fluid in the barrels may be simultaneously or individually ejected through the needles by the plungers communicating with the barrels. The plungers are moved by a single depressor. The body portion of the barrel includes an appropriately sized and shaped end member, typically curved, and adjacent the closed ends of the barrels. The end member serves to limit the depth of insertion of the needles and thereby guide the user. The end member is very important since the injections will typically be made by the users themselves, not physicians or nurses. The needles may differ in length if necessary.

Other embodiments of the invention include those having barrels with different spacing, possibly desirable because of manufacturing considerations, and single barrel designs with dual needle arrangements. These also have an end member for limiting the depth of insertion and, in turn, easing the user's task of administration by providing guidance. The end member is desirably curved in accordance with the shape of the penis.

BRIEF DESCRIPTION OF THE DRAWINGS

FIG. 1 shows an overall view of the preferred embodiment, illustrating the dual needle syringe with the two barrels slightly separated by some distance, while connected by the integrally molded housing forming the barrels. A protective cap is shown on the syringe in FIGS. 1 and 4. All illustrations are greatly enlarged to clarify details of the invention.

FIG. 2 is a top view of the embodiment shown in FIG. 1, and illustrates the shape of the depressor and its location with respect to the plungers (shown in dotted lines) below it.

FIG. 3 is a cross section of the embodiment shown in FIG. 1, and in the direction and at the location indicated in FIG. 1. FIG. 3 illustrates the configuration of the plungers and shows the protective clip attached onto the plungers, to prevent inadvertent closure of them.

FIG. 4 is a cross section of the embodiment shown in FIG. 1, in the direction and at the location indicated in FIG. 1. FIG. 4 illustrates the elevational details of the syringe, especially the barrel grip 26.

FIG. 5 illustrates the syringe in use, the needles shown injected into the penis, shown here in cross section.

FIG. 6 illustrates a different embodiment of the dual needle syringe, this one showing the barrels in a closer configuration, thereby requiring passageways from the closer barrels to the more distant, but still parallel, needles.

FIG. 7 illustrates a still further embodiment of the syringe, this one a single barrel version, but having twin, parallel needles, both of which are connected to the lower end of the barrel.

DETAILED DESCRIPTION OF THE PREFERRED EMBODIMENT

The invention is a dual hypodermic needle syringe having very fine and short needles designed to simultaneously inject the corpora cavernosa tissues in the penis. FIG. 1 illustrates an enlarged view of the subject invention with the barrels 10 shown cut away to illustrate the plungers 12 therein. Attached to the plungers are the plunger rods 14, which are simultaneously depressed by the depressor 16.

The barrels 10 may be integrally molded in one piece, joined by a central portion 24, and having an end member 18 which abuts the penis when the syringe is in use, the needles 20 then being fully inserted. The end member is shown in FIG. 1 with a curvature to approximate that of a flaccid penis. Through the end member 18 extend needles 20, shown here having identical lengths. The end member 18 may be fabricated integrally with the barrels, or may be attachable. The needles 20 are most desirably fabricated integrally, as the system is designed for throwaway operation, but they may be attachable, as needles in conventional throwaway needles typically are. The needles are shown encased by the cap 22, which snaps over the end member 18. The barrel grip 26 is shown in FIGS. 1 and 4. This grip is designed for the user's easy handling of the syringe.

FIG. 2 shows the location of the plungers 12 as viewed from the top, looking down on the depressor 16. FIG. 3, viewed at the cross-sectional direction shown in FIG. 1, shows the clip 28 inserted in place on the plunger rods 14. The clip is designed to prevent inadvertent depression of the plungers, shown below the top member 30 of the barrel body, and has small projections 52 to prevent the clip from slipping off.

FIG. 4 illustrates, at the location indicated in FIG. 1, the end view shape and differing elevation of the curved end member 18. This member is curved in the preferred embodiment, but could easily be of different contour in another embodiment.

The invention is shown in use in FIG. 5, the needles 20 shown here injected into the corpora cavernosa tissues 38 from the dorsal side of the penis. The erectile tissue of the penis, the corpus cavernosum 38 and the corpus spongiosum 40, are composed of large venous sinuses which contain relatively little blood when the penis is flaccid, but which become very dilated when blood is trapped in them. The dilation of this tissue material with blood is thus the desired objective, with the further objective of effecting and maintaining a hard erection of the organ.

Normally, an erection has two steps: first some nervous stimulation, and then vasodilation of the arteries through which blood flows in the penis. The stimulation of the nervous fibers in the penis may emanate from the central nervous system or from local stimulation of the organ. The nervous stimulation induces vasodilation of the profunda arteries 42 and the dorsal arteries 44 (FIG. 5), through which the primary erectile tissues of the penis, the corpora cavernosa 38, receive blood and gradually become engorged and, in turn, less flaccid. The corpus spongiosum 40, which surrounds the urethra 46 and is separated vascularly from the corpora cavernosa 38, also becomes engorged with blood and thus contributes to the expansion and rigidity of the organ, but its much smaller size, relative to the corpora cavernosa, renders its importance much less critical.

If the arteries are not adequately vasodilated, and if the erectile tissues and muscular structure of the penis do not adequately constrict blood flow from the corpora cavernosa and the corpora spongiosa through the deep dorsal vein 43, the subcutaneous dorsal vein 48, and the subcutaneous lateral veins 50, then some means of doing these things is necessary to effect an erection or to enhance an unsatisfactory erection. Injection of an appropriate vasodilator into the corpora cavernosa will dilate the profunda and dorsal arteries, thereby allowing much blood to come into the corpora cavernosa, engorging them into a much larger volume and significantly constricting the aforementioned veins, thereby reducing the blood flow from the penis. The result is vasodilation without physiologic nervous stimulation.

The key to injecting the appropriate drug into the penis is the use of the subject invention having the dual needles at the appropriate distance, and with the safety and convenience factor of the curved end member. Blood is thus left free to flow into the penis in the normal circulatory process, but is restricted from leaving the organ, thereby resulting in dilation of the corpora cavernosa, partial constriction of the existing veins, and thus an erection. Use of this means of alleviating the problems of impotence is far superior to other methods since it is totally unobtrusive and is something of which the female sex partner is totally unaware.

The invention is inserted into the corpora cavernosa of the penis from the dorsal side by placing the needles on either side of and approximately equidistant from the subcutaneous dorsal vein, which is easily visible. The needles are preferably inserted such that the fluid is secreted in the area of the deep arteries in the corpora cavernosa, in which case the needles should be about 6 mm long. It is possible to provide a similar effect by injection of the appropriate drug in the area of the superficial arteries, in which case the needles may be 3 to 4 mm long. The needles are preferably about 10 to 12 mm apart.

FIGS. 6 and 7 illustrate alternate embodiments of the invention, FIG. 6 showing a dual needle syringe having the barrels 32 close together, thereby necessitating a passageway to the needles 20 which remain at the optimum distance for piercing the corpora cavernosa simultaneously, such distance not to exceed the estimated two-point threshold of pain distance on the dorsal side of the penis. The plungers 12 are simultaneously depressed by the single depressor 16, but in all embodiments, individually operable depressors could be used. The end member 18 of the embodiment shown in FIG. 6 is curved to approximate the contour of the penis. FIG. 7 illustrates still another embodiment, this one showing a single barrel version of the multiple hypodermic arrangement. The needles 20 are connected by passageways through the end member 18 to the lower portion of the barrel 33. Depression of the depressor 34 results in simultaneous emission of the fluid in the barrel from the needles 20. Again, the needles are at the optimum location discussed above and may be of different lengths if desired.

In view of the prececding description of several embodiments of the invention, alternative embodiments may be apparent to those skilled in the art. Accordingly, the embodiments described and illustrated herein are to be construed as merely illustrative of the application of the principles of this invention, and for the purpose of teaching and enabling those skilled in the art to make and use the invention. The preferred embodiment of the invention described and shown herein is to be understood to be the best mode presently contemplated, but is by no means the only embodiment possible. Numerous other arrangements and modifications may be made in the syringe for use in injecting the penis without departing from the scope of this invention as defined in the following claims and all equivalents thereto. For example, the syringe may have a single barrel or may have multiple barrels, and the dual barrels may not be directly connected. Accordingly, the scope of the invention is defined by the claims and all their equivalents falling within the true spirit and scope of the invention.

What is claimed is:

1. A dual hypodermic needle syringe for injecting fluids into the penis, comprising
   two parallel, interconnected barrels, each having an open end and a closed end, each of said closed ends having a passageway therethrough;
   two parallel needles extending from said closed ends of said barrels;
   two parallel plungers communicating with said barrels;
   means for depressing both said plungers; and
   a curved end member adjacent said closed ends of said barrels, said end member being for limiting the depth of insertion of said needles, and said curvature approximately conforming to the shape of the penis.

2. The multiple hypodermic needle syringe arrangement of claim 1, wherein said means is a single depressor for simultaneously depressing both said plungers.

3. The multiple hypodermic needle syringe arrangement of claim 1, wherein said means are two independently functioning depressors for depressing both said plungers individually.

4. The multiple hypodermic needle syringe arrangement of claim 1, wherein said needles differ in length.

5. The multiple hypodermic needle syringe arrangement of claim 1, wherein said end member is curved, to approximately conform to the shape of the penis.

6. A dual hypodermic needle syringe for injecting fluids into the penis, comprising
   a single barrel having an open end and a closed end, said closed end having two passageways therethrough;
   two parallel needles extending from said closed end of said barrel and interconnected through said passageways to said barrel;
   a depressable plunger communicating with said barrel; and
   a curved end member adjacent said closed end of said barrel, said end member being for limiting the depth of insertion of said needles, and said curvature approximately conforming to the shape of the penis.

7. The multiple hypodermic needle syringe arrangement of claim 6, wherein said needles differ in length.

* * * * *